United States Patent [19]

Groeneveld et al.

[11] Patent Number: 4,554,386

[45] Date of Patent: Nov. 19, 1985

[54] PROCESS FOR THE PREPARATION OF METHYL TERTIARY BUTYL ETHER

[75] Inventors: Christiaan Groeneveld, Ransdaal; Dirk Knol, Beek; Johannes D. M. Verstegen, Sittard; Jacobus Jansen, Geleen, all of Netherlands

[73] Assignee: Stamicarbon B.V., Geleen, Netherlands

[21] Appl. No.: 595,165

[22] Filed: Mar. 30, 1984

[30] Foreign Application Priority Data

Apr. 1, 1983 [NL] Netherlands ............... 8301180
Apr. 28, 1983 [NL] Netherlands ............... 8301496

[51] Int. Cl.$^4$ ................................ C07C 41/06
[52] U.S. Cl. ..................................... 568/697
[58] Field of Search ............................ 568/697

[56] References Cited

U.S. PATENT DOCUMENTS 3,979,461 9/1976 Ancillotti et al. ............ 568/697
4,262,146 4/1981 Childs ........................ 568/697
4,423,251 12/1983 Pujado et al. ............... 568/895

FOREIGN PATENT DOCUMENTS 0042252 12/1981 European Pat. Off. .......... 568/697

Primary Examiner—J. E. Evans
Attorney, Agent, or Firm—Cushman, Darby & Cushman

[57] ABSTRACT

A process for the preparation of methyl tertiary butyl ether (MTBE) in two stages:
the first stage comprising the reaction of isobutene with methanol in the presence of an acid catalyst, yielding MTBE, while the second stage comprises firstly the conversion of normal-butenes present in the hydrocarbon flow, which remains behind after separation of the MTBE formed in the first stage into isobutene and secondly passing the mixture thus obtained to a reaction zone to form MTBE.

Optionally an extra amount of methanol can be supplied to said reaction zone. Said reaction zone can be the same as that used in the same first stage or another one.

5 Claims, 2 Drawing Figures

4,554,386

PROCESS FOR THE PREPARATION OF METHYL TERTIARY BUTYL ETHER

BACKGROUND OF THE INVENTION

The invention relates to a process for the preparation of methyl tertiary butyl ether (MTBE) by contacting an isobutene-containing hydrocarbon flow, predominantly consisting of hydrocarbons with 4 carbon atoms, with methanol in a reaction zone in the presence of a catalyst and separating the methyl tertiary butyl ether formed from the reaction mixture.

It is known to react isobutene with methanol in the presence of an acid catalyst, yielding methyl tertiary butyl ether (MTBE), for instance as described in U.S. Pat. Nos. 2,480,940 and 3,037,052. The isobutene is mostly applied in the form of $C_4$-raffinate 1, originating from the thermal or catalytic cracking of hydrocarbons. Besides isobutene, this $C_4$-raffinate 1 also contains monoalkenes and saturated hydrocarbons as well as possibly small amounts of acetylenic and dialkenic hydrocarbons, but almost no butadiene.

After the isobutene present in this $C_4$-raffinate has been reacted with methanol in the presence of a catalyst in a reaction zone, yielding MTBE, the MTBE formed is separated and the remaining $C_4$-hydrocarbon flow, also called the $C_4$-raffinate 2 and consisting mainly of n-butene and butanes, is discharged. The value of this $C_4$-raffinate 2 generally does not exceed its calorific value.

SUMMARY OF THE INVENTION

The object of the invention is to provide a process for the preparation of MTBE in which the $C_4$-raffinate 2 obtained from the MTBE reactor, after separation of the MTBE formed, is in the main used for the preparation of MTBE.

This object is accomplished by the process of the present invention, which is characterized in that the hydrocarbon flow remaining behind after separation from the reaction mixture of the MTBE formed is at least in part discharged to an isomerization unit, where normal-butene is in part converted into isobutene, and the product obtained is returned to a reaction zone where it is contacted with methanol in the presence of a catalyst.

Surprisingly, the amount of butanes in the hydrocarbon flow sent to the isomerization unit is not detrimental to the process and a separation of the light and heavy products formed upon isomerization is not required. The light products leave the process through the purge, while the heavy petrol-like products end up in the MTBE. The amounts of the heavy products being small, this additional contamination usually is allowable, for in general the specification requirements of the MTBE for use as motor fuel additive are satisfied. Depending on the purity requirements to be met by the MTBE, however, under certain recirculation conditions separation of heavy products may take place.

In an embodiment according to the invention one reaction zone will suffice, because the normal-butene converted in the isomerization unit is returned to the same reaction zone as to which the $C_4$-raffinate 1 is supplied.

It is also possible to apply two reaction zones arranged in series, as is known, for instance, from NL-A-7505991.

After the isobutene present in the $C_4$-raffinate 1 has been reacted with methanol, in the presence of a catalyst, in a first reaction zone, yielding MTBE, the MTBE formed is separated and the remaining hydrocarbon mixture, consisting mainly of normal-butenes, butanes and as yet unconverted isobutene, is sent to a second reaction zone, where the remaining isobutene, together with methanol and in the presence of a catalyst, is converted into MTBE.

Of the isobutene in the hydrocarbon mixture supplied to the first reaction zone, the larger part, approximately up to 90%, is together with methanol converted into MTBE. The remaining amount of isobutene, about 10%, is together with methanol converted into MTBE in the second reaction zone. This has the disadvantage that essentially the second reaction zone is insufficiently loaded, because a relatively small amount of isobutene is supplied. The amount of other hydrocarbons, consisting of mainly n-butenes and butanes, still requires the second reaction zone to have a certain volume, though these hydrocarbons do not yield any MTBE production. In other words, the second reaction zone actually is too large for the amount of MTBE produced in it.

According to the invention this disadvantage is eliminated in that the normal-butenes present in the mixture of non-converted isobutene, methanol and the other hydrocarbons, which remains behind after separation of the MTBE formed in a first reaction zone, is at least in part converted into isobutene and the mixture thus obtained, optionally with methanol added to it, is passed into a second reaction zone. The second MTBE reactor then is better loaded as regards the MTBE production, since the feed for this second reactor has a substantially higher isobutene content, while the total amount of feed supplied has remained virtualy the same.

The amount of $C_4$-raffinate 2 sent to the isomerization unit amounts to 20–80% of the total $C_4$-raffinate 2 flow leaving the MTBE reactor, and by preference to 40–60%.

In a practical embodiment of the process according to the invention in which the reaction zones are in separate reactors, the mixture supplied to the isomerization zone applied for the conversion of normal-butenes into isobutene, which mainly consists of non-converted isobutene, methanol, n-butenes and butanes is the top product from the MTBE separation column and is in gaseous condition, making evaporation of the feed for the isomerization superfluous. This means a substantial reduction of the energy consumption.

After the second reactor also a separation column is present, in which inter alia the butanes are separated and discharged from the process. The MTBE as well as the heavier products are recirculated to the MTBE separation column after the first reactor. The advantage of this is that a too high butane level during the process is avoided. Particularly the isomerization zone then is less loaded with these lighter components.

In general it can be stated, starting from a certain feed for the preparation of MTBE, the process according to the invention allows more MTBE to be produced from this feed.

DETAILED DESCRIPTION OF A PREFERRED EMBODIMENT

A preferred embodiment of the invention will be described with reference to the drawings and will be illustrated by examples.

Figure 1:
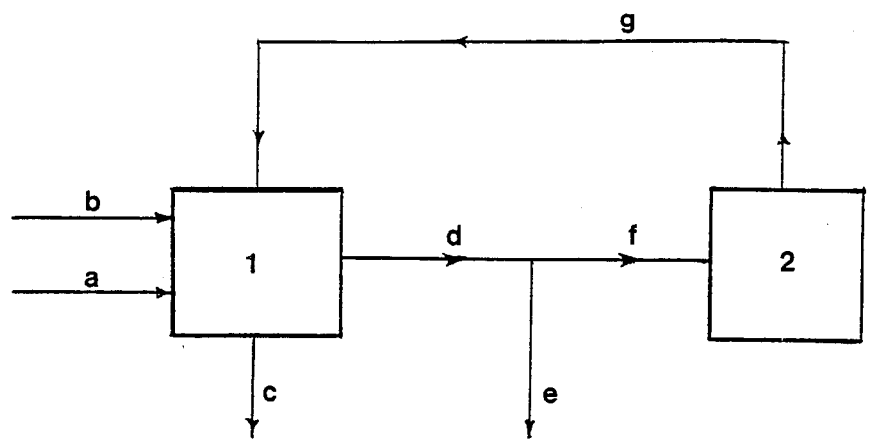
FIG. 1 is a diagram of a process in which one reaction zone is applied.

According to FIG. 1, an isobutene-containing $C_4$-hydrocarbon flow is supplied to reactor 1 through line a, while methanol is supplied through line b. In the presence of a suitable catalyst in reactor 1, MTBE is formed. The MTBE formed is discharged through line c, and the remaining $C_4$-flow, also called $C_4$-raffinate 2, through line d. Part of the $C_4$-raffinate 2 is removed from the process through purge line e, and the remaning part is passed through line f to isomerization unit 2, where normal-butene is converted into isobutene. The product obtained is returned to MTBE reactor 1 through line g.

Figure 2:
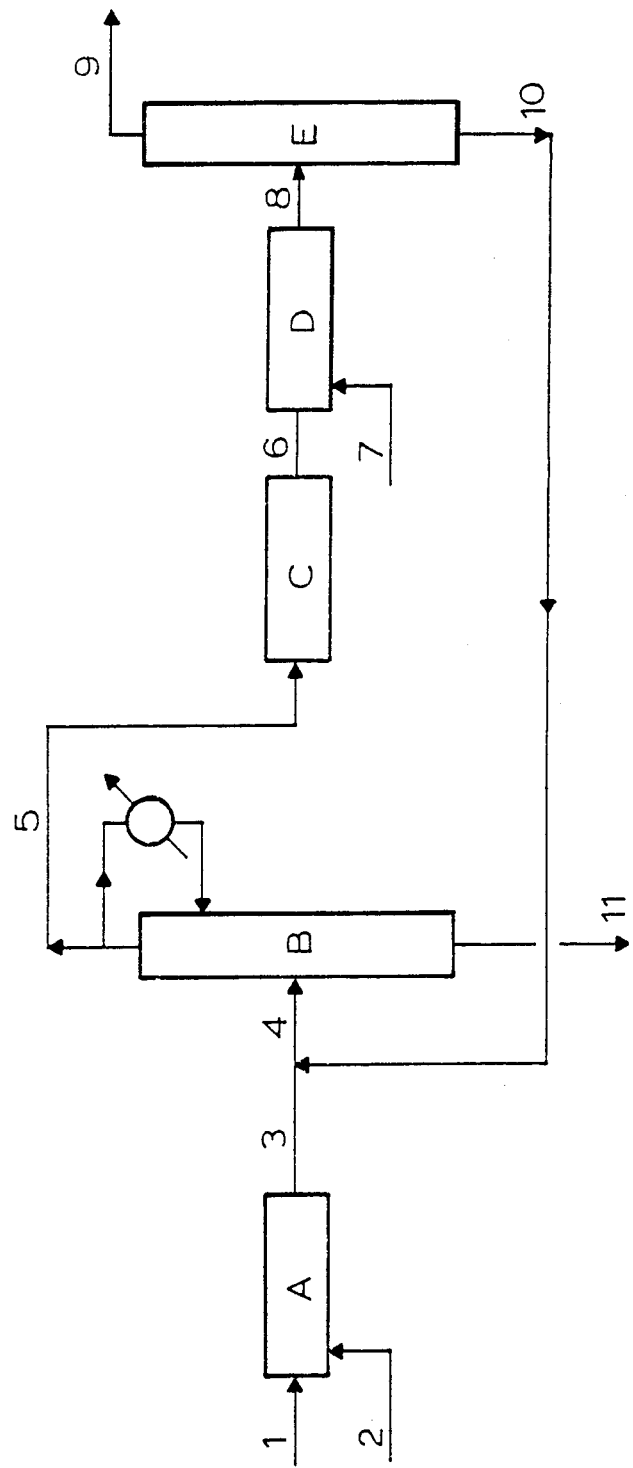
FIG. 2 is a diagram with two reaction zones connected in series.

According to FIG. 2, reactor A is supplied, through line 1, with an isobutene-containing hydrocarbon mixture consisting predominantly of hydrocarbons with four carbon atoms, and through line 2 with methanol. In the presence of a suitable catalyst, MTBE is formed in reactor A. The product formed in reactor A is sent to MTBE separation column B through line 3. From this column B, MTBE is discharged through line 11 and through line 5 non-converted isobutene and methanol as well as all other hydrocarbons from the hydrocarbon mixture fed to reactor A. These other hydrocarbons are mainly n-butenes and butanes. Line 5 leads to isomerization unit C, where the n-butenes supplied are in part converted into isobutene. The product formed in isomerization unit C is passed through line 6 to second reactor D, to which additional methanol is also supplied through line 7. From this reactor D the product formed is sent through 8 to separation column E, where two fractions are obtained, on the one hand MTBE, heavier products and part of the $C_4$-hydrocarbons, mainly n-butenes, which are returned to separation column B through lines 10 and 4, and on the other hand the lighter products with butanes, non-converted isobutene, n-butenes and methanol, which are discharged from the process through line 9. Discharging of the butanes and the lighter products from the process is necessary as otherwise these products would accumulate in the process.

EXAMPLE I
(FIG. 1)

In an MTBE reactor (1), 15.3 kg/h $C_4$-raffinate 1 (through line a), consisting of 6.0 kg isobutene, 8.0 kg n-butene and 1.3 kg butanes, was contacted with 3.4 kg/h methanol (through line b) in the presence of a catalyst. In the reactor 9.3 kg/h MTBE was formed.

After separation of the MTBE, the remaining hydrocarbon flow (d) was divided into two flows (e and f). Flow e, which amounted to 44%, was discharged from the process, and flow f (56%) was sent to an isomerization unit (2), where the n-butene present in flow f was in part converted into isobutene. The product formed in the isomerization unit (2), consisting of 2.1 kg isobutene, 4.6 kg n-butene, 1.6 kg butanes and 1.0 kg byproducts, was recirculated to the MTBE reactor (1) with simultaneous addition of 1.2 kg/h additional methanol. As a result, an additional amount of MTBE of 3.2 kg/h was formed from the recirculated isomerization product and the additionally added methanol.

COMPARATIVE EXAMPLE

In an MTBE reactor (1) an amount of $C_4$-raffinate 1 was added, as in the previous example, and contacted with an equivalent amount of methanol under the conditions described in Example I. In this reactor (1) 9.3 kg/h MTBE was formed.

EXAMPLE II
(FIG. 2)

In an MTBE reactor A, 14.9 kg/h $C_4$-raffinate 1, supplied through line 1 and consisting of 6.0 kg isobutene, 7.7 kg n-butenes and 1.2 kg butanes, was contacted with 3.3 kg/h methanol (supplied through line 2) in the presence of a catalyst. 8.4 kg/h MTBE was formed in reactor A. After separation of the MTBE in column B, the non-converted isobutene (0.6 kg/h), together with methanol (0.3 kg/h) and the remaining hydrocarbon mixture, consisting of 1.2 kg/h butanes and 8.4 kg/h n-butenes, was sent to an isomerization unit C, where part of the n-butenes supplied, viz. 2.5 kg/h, was converted into isobutene. Through line 6, the product formed was passed to second reactor D together with 1.4 kg/h methanol, which was supplied through line 7. In said second reactor 4.3 kg/h MTBE was formed. In total 12.7 kg/h MTBE was produced in both reactors.

COMPARATIVE EXAMPLE

In an MTBE reactor A an amount of $C_4$-raffinate 1 was introduced, as in the previous example, and contacted with an equivalent amount of methanol under the circumstances described in Example I. The mixture of hydrocarbons and methanol discharged from MTBE separation column B through line 5 was sent direct to MTBE reactor D. To this reactor also 0.08 kg/h additional methanol was supplied through line 7. In reactor D this time 0.8 kg/h MTBE was formed. In total 9.3 kg/h MTBE was formed in reactor A and D.

The examples given clearly demonstrate that, when using the process according to the invention and starting from the same amount of feed, a higher MTBE yield is obtained.

What is claimed is:

1. In a process for the preparation of methyl tertiary butyl ether by contacting an isobutene-containing hydrocarbon feed, predominantly consisting of hydrocarbons with four carbon atoms, with methanol in a reaction zone in the presence of a catalyst and separating the methyl tertiary butyl ether thus formed from the reaction mixture, the improvement essentially comprising the combination of steps of:

carrying out a first reaction between isobutene contained in said hydrocarbon feed and methanol in a first reaction zone in the presence of a catalyst, and separating methyl tertiary butyl ether thus formed from a first residual hydrocarbon stream containing normal-butene;

introducing at least a portion of said residual hydrocarbon stream into an isomerization zone wherein at least a portion of the normal-butene introduced therein is converted to form a second residual hydrocarbon stream containing isobutene; and introducing said second residual hydrocarbon stream, together with a further amount of methanol, into a second reaction zone, separate from said first reaction zone, wherein isobutene contained in said second residual hydrocarbon stream is reacted with said further amount of methanol in the presence of a catalyst to form a further amount of methyl tertiary butyl ether.

2. The process of claim 1 wherein said methyl tertiary butyl ether formed in said second reaction in said second reaction zone is separated from a third residual hydrocarbon stream containing butanes.

3. The process of claim 2 wherein said butanes are discharged from the process.

4. The process of claim 1 wherein from between about 20 and 80 percent of said first residual hydrocarbon stream is introduced into said isomerization zone.

5. The process of claim 1 wherein from between about 40 and 60 percent of said first residual hydrocarbon stream in introduced into said isomerization zone.

* * * * *